United States Patent [19]
Barak et al.

[11] 4,001,387
[45] Jan. 4, 1977

[54] PROCESS FOR PREPARING RADIOPHARMACEUTICALS

[75] Inventors: Morton Barak, Walnut Creek; Harry S. Winchell, Lafayette, both of Calif.

[73] Assignee: Medi-Physics, Inc., Emeryville, Calif.

[22] Filed: Jan. 2, 1975

[21] Appl. No.: 537,930

Related U.S. Application Data

[60] Division of Ser. No. 383,797, July 30, 1973, Pat. No. 3,902,849, which is a continuation-in-part of Ser. No. 173,099, Aug. 19, 1971, Pat. No. 3,749,556.

[52] U.S. Cl. .............................. 424/1; 252/301.1 R
[51] Int. Cl.² ...................................... A61K 43/00
[58] Field of Search ............... 252/301.1 R; 424/1; 23/252 R; 250/428, 429, 430, 434, 435, 436; 210/31 C, 198 C, 264, 266, 284

[56] References Cited

UNITED STATES PATENTS

| | | | |
|---|---|---|---|
| 2,487,574 | 11/1949 | Meng | 210/198 C |
| 3,462,245 | 8/1969 | Eudes et al. | 23/252 R |
| 3,466,361 | 9/1969 | Richards et al. | 424/1 |

*Primary Examiner*—Benjamin R. Padgett
*Assistant Examiner*—Deborah L. Kyle
*Attorney, Agent, or Firm*—Samuel L. Welt; Bernard S. Leon; R. Hain Swope

[57] ABSTRACT

A process for the preparation of technetium-99m labeled pharmaceuticals is disclosed. The process comprises initially isolating technetium-99m pertechnetate by adsorption upon an adsorbent packing in a chromatographic column. The technetium-99m is then eluted from the packing with a biological compound to form a radiopharmaceutical.

7 Claims, 5 Drawing Figures

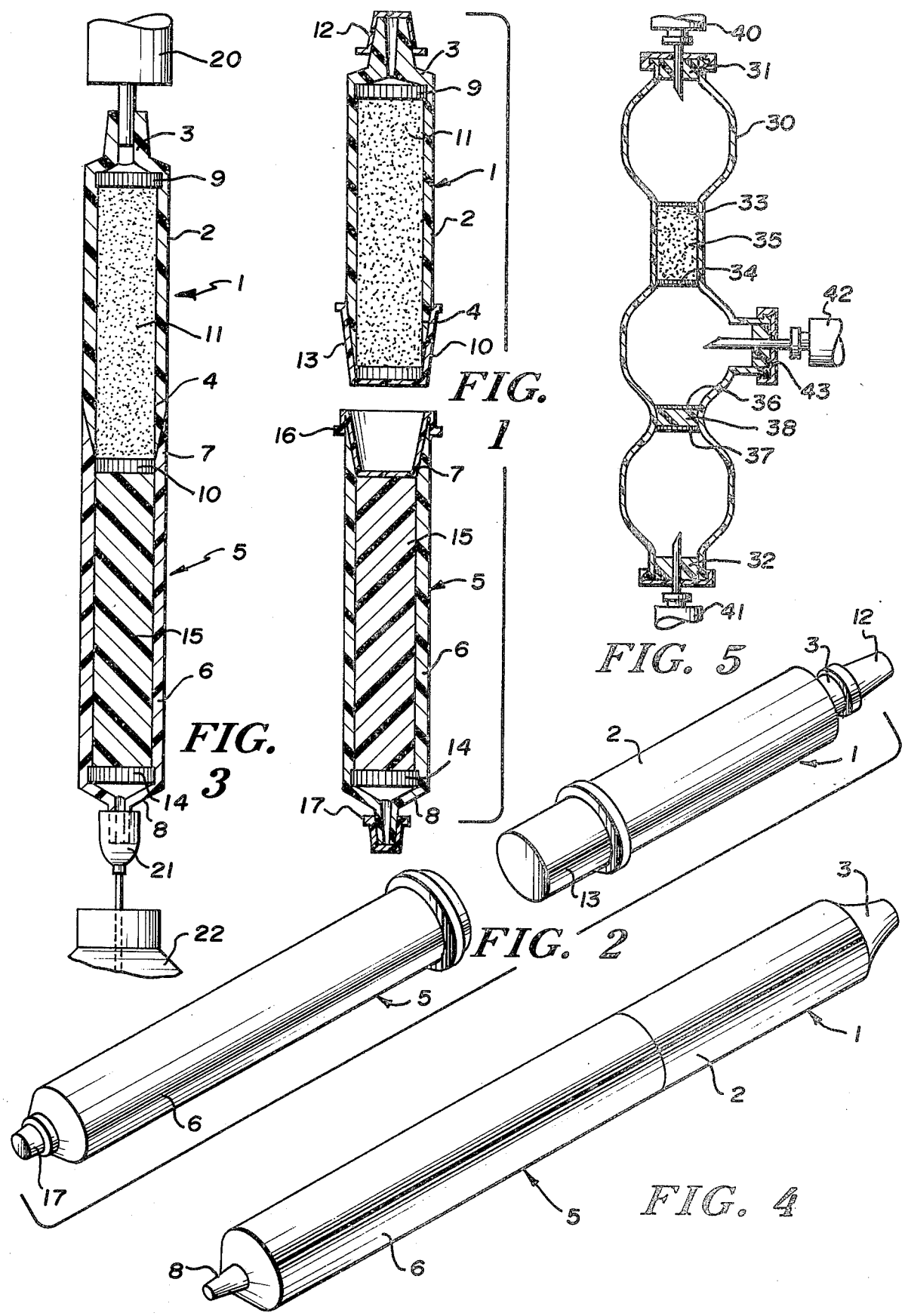

PROCESS FOR PREPARING RADIOPHARMACEUTICALS

RELATED APPLICATIONS

This application is a divisional application of U.S. patent application Ser. No. 383,797 filed July 30, 1973 now U.S. Pat. No. 3,902,849 which in turn is a continuation-in-part application of U.S. Pat. application Ser. No. 173,099 filed Aug. 19, 1971 which issued as U.S. Pat. No. 3,749,556 on July 31, 1974.

DETAILED DESCRIPTION OF THE INVENTION

This invention relates generally to production and use of radioisotopes and more particularly to simple apparatus and methods for producing contaminant-free technetium-99m eluates of specific concentration and technetium-99m labeled radiopharmaceuticals.

The object of this invention is to provide a simple two-step process for making techentium-99m solutions of specific concentration or technetium-99m labeled pharmaceuticals quickly and without the need for a skilled chemist or pharmacist.

An object of this invention is to provide simple apparatus and methods for isolating technetium-99m by adsorbing it upon a packing material and then releasing it to a chelating eluant to produce technetium-99m solutions of specific concentration or to produce directly-labeled radiopharmaceuticals.

Still another object of this invention is to provide apparatus and methods which employ an adsorbent packing of reducing agent for technetium-99m pertechnetate to isolate and concentrate it to any desired level of radioactivity so that solutions and radiopharmaceuticals of known specific concentrations of radioactivity can be made.

An object of this invention also is to provide simple methods and apparatus for eliminating chemical and radionuclidic contaminants from the processed radiopharmaceutical and technetium-99m solutions.

Other objects and advantages will become apparent from a consideration of the following description and the accompanying drawings wherein FIG. 1 is a cross-sectional view of the components of the kit of this invention prior to assembly;

FIG. 2 is a perspective view of the kit of this invention shown in FIG. 1 before assembly;

FIG. 3 is a vertical sectional view of the kit of this invention assembled for generation of a radiopharmaceutical;

FIG. 4 illustrates in perspective the assembled kit of FIG. 3; and

FIG. 5 is a cross-sectional view of an improved radioiostope generator of this invention.

This invention includes procedures and apparatus for making technetium-99m solutions and pharmaceuticals labeled with technetium-99m which are useful in nuclear medicine for organ imaging. As used herein the term "biological compounds" includes single elements, chemical compounds, mixtures of either or both or complexes of other sorts which are physiologically benign chelating agents for reduced technetium-99m that may be administered internally or otherwise without adverse effects to living organisms, particularly to human beings.

The technetium-99m isotope is conveniently available in isotonic solution in the form of chemically stable pertechnetateion ($TcO_4$)$^-$. Sodium pertechnetate solutions usually are eluted by saline solution in generators or "cows" from the longlived parent molybdenum-99. The inherent chemical properties of technetium-99m and a number of undesirable characteristics of pertechnetatesolutions originating from such generators normally require time consuming and complicated chemical processing performed by skilled chemists or pharmacists with substantial radiation exposure to make useful technetium-99m labeled pharmaceuticals.

The "cow" eluate frequently contains variable amounts of non-radioactive contaminants such as aluminum and molybdenum ions. It often contains as well, variable amounts of longlived radionuclidic impurities such as $^{99}$Mo, the parent isotope, and neutron activation and fission products such as $^{134}$cesium, $^{95}$Zr $^{95}$Nb, $^{124}$Sb, $^{60}$Co or $^{46}$Sc. The specific concentration of $^{99m}$Tc obtained from the "cow" also varies considerably. The improved radioiostope generator and generating method of this invention eliminate a number of the difficulties heretofore encountered in the eluate of prior art methods and means for producing technetium-99m in usable form.

$^{99m}$Tc in the chemical form of pertechneate ($TcO_4$) ion is commonly used to image some areas of the body. But due to the imperfect nature of its biological distribution as the pertechneate ion, drugs such as perchlorate or iodide ion or atropine are often administered to the patient to suppress uptake in areas that might interfere with scan interpretation or reduce radiation dose to uninvolved organs. For example before $^{99m}$Tc pertechnate is given for brain scanning, relatively large amounts of the aforementioned suppressive drugs are administered to the patient to suppress characteristic uptake in the salivary glands and choroid plexus-events that might interfere with scan interpretation. Thyroid uptake is suppressed as well, thus rescuing this organ from an otherwise gratuitous radiation dose.

It is therefore beneficial to combine $^{99m}$Tc with substances which result in a radiopharmaceutical that has a more specific affinity for the organ of interest and a reduced tendency to concentrate elsewhere. For example, $^{99m}$TcO$_4$ treated with an iron salt plus ascorbic acid, results in a radiopharmaceutical that concentrates in the cortex of the kidney to such a degree that usefully informative scintiphotographs may be taken of that organ. Other preparations of $^{99m}$Tc labeled compounds are useful for liver and lung imaging and for placenta localization. Almost all of the chemical processes required to convert pertechnetate ion to useful pharmaceuticals are time consuming and complex. They require services of a skilled radiochemist and substantial radiation exposure.

THE RADIOPHARMACEUTICAL GENERATOR KIT

The radiopharmaceutical generator kit disclosed in FIGS. 1 and 2 assembles into what is essentially a small chromatographic column illustrated in FIGS. 3 and 4. The kit includes a first tubular section referred to generally as 1. It has an elongated tubular shell 2; and integral liquid inlet 3 at one end, such as the illustrated female luer slip fitting; and at the other end a first joinder means 4, such as the illustrated male taper which assembles to a corresponding taper in the second tubular section referred to generally as 5.

The second tubular section 5 includes an elongated tubular shell 6; a second joinder means 7 at one end, such as the female taper 7 for quick and vacuum-tight assembly to male taper 4 of the first tubular section of the kit as is shown in FIG. 3; and at the other end an integral liquid outlet 8 such as illustrated male luer slip fitting. A first inert porous disc 9 and a second inert porous disc 10 define with shell 2 a first processing zone within the first tubular secion 1 which is packed with a particulate or sintered reducing agent 11 for technetium-99m pertechnetate. The porous disc 9, 10 may be inert coarse filters press-fit into shell 2 or one of them, such as porous disc 9 may be integrally molded with the shell from linear polyethylene or polypropylene or other physiologically and chemically inert materials. The pore size permits liquid flow but confines the reducing agent packing within the first processing zone. Porous disc 10 press-fits into shell 2 after reducing agent 11 is packed. The reducing agent for technetium-99m pertechneate is a particulate metal powder or sinter which is aseptically packed dry and dry heat sterilized. Plastic caps 12 and 13 over each of its ends, seal the first tubular section 1 and preserve sterility until its use.

The second tubular section 5 carries a third porous disc 14 at its lower end adjacent to liquid outlet 8. This disc has a pore size in the order of 5 microns in diameter. It may be molded integrally with a polyethylene or polypropylene shell 6 or may be press-fit filter material such as nylon, Teflon, sintered stainless steel or a glass frit. Shell 6 between the end of female taper 7 and porous disc 14 defines a second processing zone packed with a cation exchange resin 15. Such resins normally are autoclave sterilized and stored wet. Plastic caps 16 and 17 close the ends of the second tubular section 5 of the kit and preserve sterility until its use.

For use in processing a radiopharmaceutical, protective plastic caps 12, 13, 16 and 17 are stripped from the kit components and the first and second tubular sections are assembled into a complete column as is illustrated in FIG. 3. The joint between the tapered joinder means 4 is vacuum tight. Liquids to be processed through the column are introduced through inlet 3 by means of hypodermic syringe 20. They are moved or assisted through the column by needle 21 attached to outlet 8 and affixed to vacuum bottle 22.

For the examples described herein tubular shells 2, 6 were 7 – 8 millimeters in inside diameter and defined first and second processing zones about 10 centimeters long. While the precise dimentions are not critical, the first processing zone must provide enough reducing agent packing and residence time to adjust the pH of the eluant during the second processing step and to buffer it to physiologically acceptable levels within the range of 5 8. On the other hand, the second processing zone must provide enough cation exchange resin and residence time to remove all uncombined reducing agent and radioisotope-carrier ions.

The Process and Pharmaceutical Products

The described kit is used to generate radioisotope labeled pharmaceuticals by a simple two-step procedure. In a first step hypodermic syringe 20 of an appropriate size introduces the labeling technetium-99m pertechnetate dispersed in a first carrier liquid, such as normal saline solution, to the column through inlet 3 to the first processing zone packed with particulate reducing agent 11. The particulate reducing agent is a metal more electronegative than hydrogen, such as iron. Needle 21 and vacuum bottle 22 assist the syringe contents to pass through the column.

The reducing agent 11 adsorbs or isolates substantially all of the technetium-99m in the intial portion of the zone — with the dimensions described, within the first one-fourth inch of the packing. Substantially all of the radioactivity collects upon this portion of the packing regardless of the concentration of the technetium-99m pertechnetate in the first carrier liquid or the quantity of the carried liquid put through the column. Thus, as much radioactivity as is desired may be concentrated on the initial portion of the reducing agent packing. The total amount of trapped radioactivity can be measured directly by its radiation. The first carrier liquid passes through the column and collects in vacuum bottle 22 stripped of substantially all of its radioactive component. With it pass all chemical and radionuclidic impurities in the "cow" eluate that do not adhere to the column packing materials.

In a second step another hypodermic syringe introduces a known volume of special eluant to the column assisted by a second sterile vacuum bottle 22 affixed to needle 21 at the bottom of the column. The eluant is a physiologically benign second carrier liquid carrying a dispersion, either in solution or suspension, of a biological compound that combines irreversibly with the reduced technetium-99m residing on the reducing agent packing in the initial portion of the first processing zone. The biological compound may be one of a group of instantly labeled chelating agents including albumin which are known to concentrate in particular human organs of interest in predictable amounts. It should be effective at physiolgical ion concentration (about 150 meq per liter) and should not precipitate or form large particles during passage through the column. The pH of the special eluant is adjusted as required to provide the requisite environment for combination of the biological compound and redcued technetium-99m. The pH of the special eluant initially should be less than 6.

The eluant carries the biological compound, now labeled with technetium-99m through the remainder of the first processing zone wherein its reaction with the reducing agent packing adjust the pH to and buffers it at physiologically acceptable levels, in the pH range of 5 – 8 for example. The second carrier liquid and its dispersion then passes through the second processing zone packed with cation exchange resin. A strongly acidic cation exchange resin composed of nuclear sulphonic acid exchange groups attached to a styrene-divinylbenzene polymer lattice is used. The resin is sodium cycled so that physiologically benign sodium ions are substituted for any uncombined reducing agent or radioisotope or other cations present in the passing eluant.

Pharmaceuticals of desired specific concentration are made by eluting the column in the second step with a volume of eluant that corresponds to the measured amount of radioactivity isolated in the first zone packing. Typical process parameters are shown in the following examples.

EXAMPLE I

TECHNETIUM-99M-IRON ASCORBIC ACID COMPLEX

A technetium-99m iron ascorbic acid complex of the type often used for kidney imaging has been generated by the process and kit described in 5 to 10minutes by a non-skilled technician. The first zone of the kit was packed with about 6 grams of 325 mesh (U.S. seive size) powdered iron. The second zone was packed with about 8 cc. (wet) of 100 – 200 mesh sodium cyclated cation exchange resin, such as AG50W-X8 manufactured by Bio Rad Company of Richmond, Calif.

About 10 cc. of a normal saline solution carrying pertechnetate ions eluded directly from $^{99}$Mo "cow" at a radioactivity concentration of about 2 millicuries per cc. was introduced by syringe to the assembled kit in a first step. This material was run through the column at a slow rate on the order of one-tenth cc. per second. Ninety-nine percent of the original radioactivity adhered to the first 1 to 2 millimeters of powdered iron in the first zone of the column.

Then a second syringe introduced to the column 4 milliliters of 0.15 normal aqueous ascrobic acid solution. The net yield of technetium-99m labeled pharmaceutical was 55 percent of the total technetium-99m activity initially present in the "cow" eluate.

The biological distribution of the resulting pharmaceutical in rats 3 hours after intravenous injection was 8 percent in the kidneys, 53.7 percent in the urine-bladder and 3.5 percent in the liver.

EXAMPLE II

TECHNETIUM-99M-IRON-ALBUMIN COMPLEX

A new technetium-99m-iron serum albumin complex has been generated in 5 – 10 minutes which concentrates in the liver and is useful for liver imaging.

Six grams of 100 mesh (U.S. seive size) hydrogen reduced iron pack the first zone of the kit and 8 cc. of sodium cycled cation exchange resin as in Example I pack the second zone. Ten cc. of the saline pertechnetate solution as used in Example I was introduced to the kit in a first step as in Example I. The pertechnetate trapping efficiency was about 92 percent. In a second step 4 milliliters of eluant comprising ten milligrams per milliliter of bovine serum albumin dissolved in 0.6 normal hydrochloric acid was then introduced to the column.

The net yield of technetium-99m labeled pharmaceutical was 55 percent of the total technetium-99m activity initially present in the "cow" eluate. Combined iron in the effluent pharmaceutical from the column was 0.35 milligrams of elemental iron per milliliter or a total of 1.4 milligrams. Biological distribution in rats one half hour after intravenous injection was 69.5 percent in the liver and 1.0 percent in the spleen. There was no reaction to the foreign protein.

This pharmaceutical is unique in its composition. It is an albium-technetium-99m-iron complex which, if particulate, has a particle size of less than 0.22 microns. In this state the complex is useful for liver imaging.

Application of heat, for example heating the pharmaceutical at 100° F. for 5 minutes, agglomerates the complex into particles barely visible to the naked eye. These particles averaging 20 – 100 microns in size concentrate in the lungs like known technetium-99m labeled macro-aggregated human serum albumin.

EXAMPLE III

TECHNETIUM-99M TIN COLLOID COMPLEX

A technetium-99m labeled tin colloid for use in liver imaging was similarly prepared in 5 – 10 minutes. The packing in the first zone was tin powder of greater than 325 (U.S. sieve size) with the same cation exchange resin and saline solution of pertechnetate ions as in Examples I and II. The trapping efficiency for the pertechnetate ion was 98.8 percent.

In a second step 4 milliliters of two normal hydrochloric acid was eluted through the column to yield 74.5 percent of technetium-99m labeled pharmaceutical based on the original technetium-99m activity in the "cow" eluate. A high concentration in the liver of experimental rats is observed after intravenous injection.

The radiopharmaceuticals listed below have been prepared using the described procedures and kit with satisfactory yields. They have useful biological distributions and are physiologically benign.

| Reducing agent packing | Eluant | Organ of greatest concentration |
| --- | --- | --- |
| Iron | Ascorbic Acid | Kidney, bladder |
| " | Citric Acid | & " |
| " | Diethylene triamine pentacetic acid | " |
| " | Salicylic Acid | " |
| " | Glycine | & Liver |
| " | HCl + Serum Albumin | " |
| " | HCl + Serum Albumin + Heat | Lungs |
| Tin | HCL | Liver |
| Mg | Ascorbic Acid | Same as TcO$_4^-$ |

THE RADIOIOTOPE GENERATOR AND PROCESS

Most commonly used radioiostope generators utilize an aqueous eluant to separate the desirable daughter isotope from the parent isotope (e.g., $^{99m}$Tc cows). The eluate from these generators has two inherent deficiencies: (1) uncontrollable, variable specific concentration and (2) variable contamination with undesirable chemicals and radionuclides arising from the processed parent isotope and its adsorbent.

The principles described for production of immediately labeled radiopharmaceuticals may be employed to correct the two dificiencies and confer additional benefits described below.

FIG. 5 illustrates a typical radioisotope generator of this invention. It is essentially a chromatographic column similar to that of the described radiopharmaceutical generator kit. While a specific embodiment of the generator is illustrated in FIG. 5 its construction also could be appropriate modifications of those generators disclosed in Gemmil U.S. Pat. No. 3,566,124 or Baumann et al, U.S. Pat. No. 3,564,256 or Ogier et al, U.S. Pat. No. 3,446,965 or Montgomery U.S. Pat. No. 3,655,981 or Shumate U.S. Pat. No. 3,535,085, etc.

The generator includes a configured shell 30 with a first inlet 31 closed, for example, by a rubber stopper and an outlet 32 closed by rubber stopper. A first porous disc 33 and a second porous disc 34 in the shell define between them a first packed zone 35 containing an ion exchange medium such as alumina upon which a parent radioisotope, for example molybdenum-99 is adsorbed. Third porous disc 36 and a fourth porous disc 37 in the shell define a second packed zone 38 which contains an adsorbent packing to adsorb the daughter radioisotope but not its parent or contaminants that may be eluted from the first packed zone 35. The adsorbent packing may be an ion exchange resin or a reducing agent for the daughter radioisotope. The porous discs 33, 34, 36 and 37 may be inert coarse filters fit into the generator shell 30. The pore size permits liquid flow but confines the packing within the two zones 35, 38.

A first eluant is introduced, for example through syringe 40 which pierces the stopper at inlet 31. The first eluant removes the daughter radioisotope from the first packed zone 35 and quantitatively deposits it in second packed zone 38 and the first eluant stripped of daughter radioisotope activity is removed from the column, for example, by syringe 41 which pierces the stopper at outlet 32. The first eluant removed by syringe 41 may be continuosly recycled to syringe 40 during elution. The adsorbent packing in second zone 38 selectively collects and concentrates the daughter radioisotope but passes all chemical and radionuclidic impurities. If the first eluant is continuously recycled, the equilibrium activity of the daughter isotope will always be present and available in second packed zone 38.

Then a second eluant is introduced, for example, by syringe 42 through the stopper at a second inlet 43. The volume of the second eluant is measured to yield the desired final specific concentration of daughter radioisotope activity. This second eluant passes only through the adsorbent packing in zone 38 and separates the collected, purified daughter radioisotope from the adsorbent packing for subsequent removal, for example, by another syringe 41 at outlet 32.

An example of use employs $^{99}$Mo as the parent isotope adsorbed onto an ion exchange agent of alumina packed into first zone 35. The first eluant introduced through the first inlet 31 by a syringe 40 is sterile, pyrogen-free normal saline solution. The daughter radioisotope, $^{99m}$Tc elutes from the alumina packing in zone 35 and collects on the adsorbent packing in second zone 38 which may be a reducing metal for technetium like iron, tin or magnesium or an ion exchange resin with or without reducing properties.

The second eluant which separates the collected $^{99m}$Tc from packed zone 38 consists of a solution having properties selected for removal of the daughter radioisotope from the zone. For example, when a reducing metal is used in packed zone 38, an aqueous acidic solution such as one of those set forth in the table following Example III may be used. The aqueous acid eluant carries the reduced daughter radioisotope through the remainder of the second packed zone 38 wherein reaction of the acid with the reducing agent packing adjusts the pH to and buffers it at physiologically acceptable levels. When the adsorbent packing in zone 38 is anion exchange resin such as Bio Rad catalog AGl-X8, which is composed of quaternary amine exchange groups attached to a styrene-divinylbenzene copolymer lattice, useful second eluants are saturated solutions of potassium iodide or thiocyanate.

The above examples and the described apparatus and procedures are for illustrative purposes only. It will be apparent to those skilled in the art that other radioisotopes and labeled pharmaceuticals may be similarly prepared and the process parameters may be modified within the scope of the invention defined in the following claims.

We claim:

1. A process for making a technetium-99m labeled pharmaceutical comprising:

selectively adsorbing and simultaneously reducing technetium-99m pertechnetate upon a particulate reducing agent comprising a metal more electronegative than hydrogen and eluting the reduced technetium-99m from said reducing agent by combination with a physiologically benign chelating agent for reduced technetium-99m dispersed in a physiologically benign liquid carrier having an initially acidic pH.

2. The process in accordance with claim 1 wherein said reducing agent is selected from the group consisting of iron, tin and magnesium.

3. The process in accordance with claim 1 wherein said chelating agent is selected from the group consisting of ascorbic acid, citric acid, diethylene triamine pentacetic acid, salicylic acid, glycine, hydrochloric acid, and mixed hydrochloric acid and serum albumin.

4. In a process for making a technetium-99m labeled pharmaceutical the steps of:

a. defining in series a first zone packed with a particulate reducing agent for technetium-99m pertechnetate comprising a metal more electronegative than hydrogen and a second zone packed with a cation exchange resin;
   b. introducing to said first packed zone technetium-99m pertechnetate dispersed in a physiologically benign carrier liquid;
   c. selectively absorbing and simultaneously reducing said technetium-99m pertechnetate upon said reducing agent in a first portion of said first zone, said carrier liquid passing completely through said first and second packed zones;
   d. eluting the reduced technetium-99m from said reducing agent by combination with a physiologically benign chelating agent for reduced technetium-99m dispersed in an acidic physiologically benign carrier liquid;
   e. raising the pH of said acidic carrier liquid and buffering it to physiological levels by passing it and the chelated technetium-99m dispersed therein through the remainder of said first zone; and
   f. passing the technetium-99m dispersion through the second zone to substitute physiologically benign cations for uncombined ions of said reducing agent and technetium-99m.

5. The process in accordance with claim 4 wherein said reducing agent is selected from the group consisting of iron, tin and magnesium.

6. The process in accordance with claim 4 wherein said chelating agent is selected from the group consisting of ascorbic acid, citric acid, diethylene triamine pentacetic acid, salicylic acid, glycine, hydrochloric acid, and mixed hydrochloric acid and serum albumin.

7. The process in accordance with claim 4 wherein said dispersion of technetium-99m pertechnetate comprises the eluate from a technetium-99m generator.

* * * * *